United States Patent
Savord

(10) Patent No.: US 11,213,855 B2
(45) Date of Patent: Jan. 4, 2022

(54) CAPACITIVE MICROMACHINED ULTRASONIC TRANSDUCERS WITH INCREASED PATIENT SAFETY

(71) Applicant: KONINKLIJKE PHILIPS N.V., Eindhoven (NL)

(72) Inventor: Bernard Joseph Savord, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 490 days.

(21) Appl. No.: 15/750,604

(22) PCT Filed: Aug. 11, 2016

(86) PCT No.: PCT/EP2016/069136
§ 371 (c)(1),
(2) Date: Feb. 6, 2018

(87) PCT Pub. No.: WO2017/025598
PCT Pub. Date: Feb. 16, 2017

(65) Prior Publication Data
US 2019/0015871 A1    Jan. 17, 2019

Related U.S. Application Data

(60) Provisional application No. 62/203,533, filed on Aug. 11, 2015.

(30) Foreign Application Priority Data

Sep. 1, 2015  (EP) ..................................... 15183223

(51) Int. Cl.
*B06B 1/02*  (2006.01)
*A61B 8/12*  (2006.01)
(Continued)

(52) U.S. Cl.
CPC .............. *B06B 1/0292* (2013.01); *A61B 8/12* (2013.01); *A61B 8/4483* (2013.01);
(Continued)

(58) Field of Classification Search
None
See application file for complete search history.

(56) References Cited

U.S. PATENT DOCUMENTS 5,997,479 A   12/1999  Savord et al.
6,013,032 A   1/2000   Savord
(Continued)

FOREIGN PATENT DOCUMENTS

JP    2007244687 A   9/2007
JP    2009148424 A   7/2009
(Continued)

OTHER PUBLICATIONS

Vaishnavi et al "Design and Analysis of Level Shifter in High Voltage Transmitter" International Journal of Scientific and Research Publications, vol. 4, Issue 1, Jan. 2014.

*Primary Examiner* — Yi-Shan Yang

(57) ABSTRACT

An array of CMUT cells has a DC bias voltage (VB) coupled to the membrane and floor electrodes of the cells to bias the electrode to a desired collapsed or partially collapsed state. The low voltage or ground terminal of the DC bias supply is coupled to the patient-facing membrane electrodes and the high voltage is applied to the floor electrodes. An ASIC for controlling the CMUT array is located in the probe with the array. The ASIC electronics are electrically floating relative to ground potential of the ultrasound system to which the CMUT probe is connected. Control and signal lines are coupled to the CMUT probe by level shifters which translate (Continued)

signals to the floating potential of the ASIC and provide DC isolation between the CMUT probe and the ultrasound system.

17 Claims, 6 Drawing Sheets

(51) Int. Cl.
    *A61B 8/00*         (2006.01)
    *G01N 29/24*      (2006.01)

(52) U.S. Cl.
    CPC ...... *G01N 29/2406* (2013.01); *B06B 2201/51* (2013.01); *B06B 2201/76* (2013.01)

(56) References Cited

U.S. PATENT DOCUMENTS

| | | |
|---|---|---|
| 6,283,919 B1 | 9/2001 | Roundhill |
| 6,328,697 B1 | 12/2001 | Fraser |
| 6,443,896 B1 | 9/2002 | Detmer |
| 6,458,083 B1 | 10/2002 | Jago et al. |
| 6,530,885 B1 | 3/2003 | Entrekin et al. |
| 6,623,432 B2 | 9/2003 | Powers et al. |
| 9,132,693 B2 | 9/2015 | Klootwijk |
| 2002/0101285 A1* | 8/2002 | Chatwin ............... H03F 3/4508 330/254 |
| 2002/0120193 A1* | 8/2002 | Chiang ............... G01S 15/8927 600/439 |
| 2005/0200241 A1* | 9/2005 | Degertekin ........... B06B 1/0292 310/334 |
| 2008/0304729 A1* | 12/2008 | Peszynski ............ A61B 8/4236 382/131 |
| 2010/0168583 A1* | 7/2010 | Dausch ................ A61B 8/4488 600/466 |
| 2010/0207484 A1 | 8/2010 | Chang |
| 2011/0084746 A1* | 4/2011 | Llewellyn ............ H03K 17/164 327/170 |
| 2012/0133005 A1* | 5/2012 | Langeries ............ B06B 1/0292 257/416 |
| 2013/0064035 A1* | 3/2013 | Kandori ................ B06B 1/0207 367/7 |
| 2014/0144240 A1 | 5/2014 | Barlow et al. |
| 2014/0257107 A1* | 9/2014 | Rice .................... A61B 8/4483 600/459 |
| 2014/0360272 A1* | 12/2014 | Kandori ................ B06B 1/0292 73/643 |
| 2015/0016221 A1* | 1/2015 | Takeuchi .............. B06B 1/0292 367/87 |
| 2015/0032002 A1 | 1/2015 | Rothberg et al. |
| 2016/0183917 A1* | 6/2016 | Kameishi ............. B06B 1/0215 600/437 |
| 2016/0199030 A1* | 7/2016 | Patil ...................... H02N 1/006 600/459 |
| 2016/0302767 A1* | 10/2016 | Gemma ............... B06B 1/0292 |
| 2017/0165715 A1* | 6/2017 | Sudol .................... B06B 1/0292 |
| 2017/0320091 A1* | 11/2017 | Budzelaar ........... A61B 8/4483 |

FOREIGN PATENT DOCUMENTS

| | | |
|---|---|---|
| JP | 2015073793 A | 4/2015 |
| WO | 2014013394 A1 | 1/2014 |

* cited by examiner

CAPACITIVE MICROMACHINED ULTRASONIC TRANSDUCERS WITH INCREASED PATIENT SAFETY

This application is the U.S. National Phase application under 35 U.S.C. § 371 of International Application No. PCT/EP2016/069136, filed on Aug. 11, 2016, which claims the benefit of U.S. Provisional Application Ser. No. 62/203,533, filed Aug. 11, 2015 and EP Application Serial No. 15183223.5 filed Sep. 1, 2015. These applications are hereby incorporated by reference herein.

FIELD OF THE INVENTION

This invention relates to medical diagnostic ultrasonic imaging and, in particular, to ultrasonic transducer probes which use capacitive micromachined ultrasonic transducers (CMUTs).

BACKGROUND OF THE INVENTION

Traditionally, ultrasonic transducers are formed of piezoelectric ceramic materials such as PZT or of piezoelectric polymers such as PVDF. Recently it has been shown that transducers can be made by semiconductor processes. Such transducers are formed of tiny semiconductor cells in which a vibrating membrane generates and receives the ultrasonic energy and are referred to as micromachined ultrasonic transducers (MUTs.) Two such transducer types are those which utilize a piezoelectric material on the membrane called piezoelectric micromachined ultrasonic transducers (PMUTs) and those which utilize a capacitive effect between a conductive membrane and another electrode called capacitive micromachined ultrasonic transducers (CMUTs.) Individual transducer elements may be formed of dozens or hundreds of such MUT cells operating in unison. Since these cells are very small, each MUT cell only produces or responds to a small amount of acoustic energy. To improve the sensitivity of a CMUT a DC bias voltage is applied across the two electrodes to bias the moving membrane electrode into close proximity with the other electrode. This will enable a relatively smaller signal to vibrate the membrane on transmit, and a small ultrasound signal to develop a relatively large capacitive variation on receive. Conventionally a high DC bias voltage is applied to the moving membrane electrode at the top of the CMUT, and the other electrode on the base of the CMUT is grounded to provide this biasing potential. To protect the patient from the high bias voltage at the top of a CMUT array, the array is covered with an insulating material such as an acoustic lens which separates the high voltage on the membrane electrodes from the skin of the patient during use of a CMUT ultrasound probe. However the lens material can become worn during use and can possibly develop surface cracks in the material with age. A crack which is deep enough to reach the membrane electrodes can thus expose the patient to the hazard of a high voltage. Accordingly it is desirable to employ measures which protect the patient from this possible hazard and improve the patient safety of a CMUT probe.

It is an objective of the present invention to improve the patient safety of a CMUT transducer to safeguard against exposure to high operating voltages of the transducer. It is a further objective to prevent exposure of a patient to high voltages in the event of cracking or other failures of the protective lens covering of a CMUT probe.

SUMMARY OF THE INVENTION

In accordance with the principles of the present invention, the bias voltage of an ultrasonic CMUT cell array is applied with a low voltage or ground coupled to the top membrane electrodes of the array and a high voltage coupled to the bottom electrode. In a preferred implementation a control integrated circuit is located below the bottom electrode and the electronics of this circuit is electrically floated relative to the electronics of the ultrasound system to which the CMUT probe is connected. In order to couple signals between the CMUT array and its integrated circuit, a level shifter is used which prevents DC coupling through the signal lines and causes the signals in the probe to be referenced to a floating electrical baseline.

BRIEF DESCRIPTION OF THE INVENTION

DETAILED DESCRIPTION OF THE EMBODIMENTS

Figure 1:
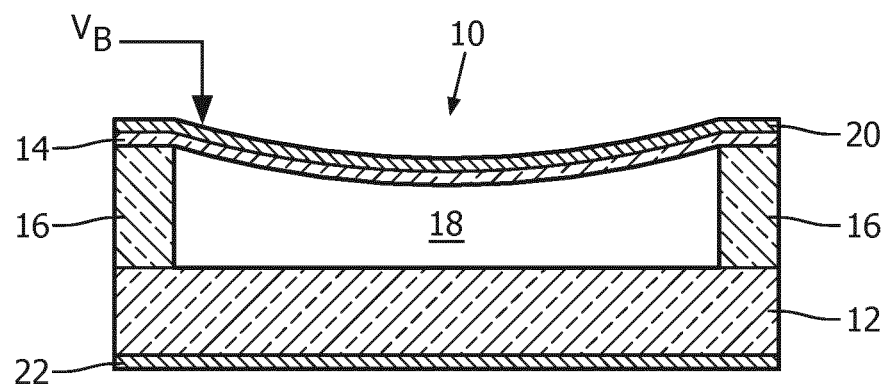
FIG. 1 is a cross-sectional view of a typical suspended membrane CMUT transducer cell.

CMUTs were initially constructed to operate in what is now known as a suspended or "uncollapsed" mode. Referring to FIG. 1, a typical uncollapsed CMUT transducer cell 10 is shown in cross-section. The CMUT transducer cell 10 is fabricated along with a plurality of similar adjacent cells on a substrate 12 such as silicon. A diaphragm or membrane 14 which may be made of silicon nitride is supported above the substrate by an insulating support 16 which may be made of silicon oxide or silicon nitride. The cavity 18 between the membrane and the substrate may be air or gas-filled or wholly or partially evacuated. A conductive film or layer 20 such as gold forms an electrode on the diaphragm, and a similar film or layer 22 forms an electrode on the substrate. These two electrodes, separated by the dielectric cavity 18, form a capacitance. When an acoustic signal causes the membrane 14 to vibrate the variation in the capacitance can be detected, thereby transducing the acoustic wave into a corresponding electrical signal. Conversely, an a.c. signal applied across the electrodes 20,22 will modulate the capacitance, causing the membrane to move and thereby transmit an acoustic signal. A DC bias voltage $V_B$ from a DC bias voltage supply is also applied across the electrodes, drawing the membrane and its top electrode 20 into close proximity with the floor of the cavity of the cell to increase sensitivity.

Figure 2:
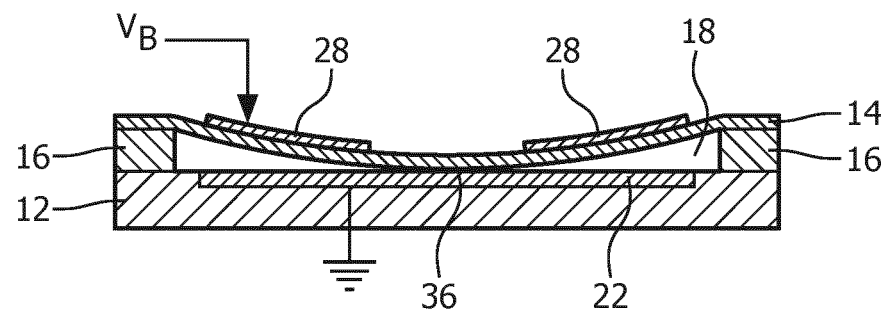
FIG. 2 is a cross-sectional view of a CMUT cell being operated in the collapsed mode.

FIG. 2 is a schematic cross-section of a CMUT cell which is operated in the collapsed mode. The CMUT cell includes a substrate layer 12 such as silicon, a substrate electrode 22, a membrane layer 14, and a membrane electrode ring 28. In this example, the electrode 22 is circularly configured and embedded in the substrate layer 12. In addition, the membrane layer 14 is fixed relative to the top face of the substrate layer 12 and configured/dimensioned so as to define a spherical or cylindrical cavity 18 between the membrane layer 14 and the substrate layer 12. The cell and its cavity 18 may define alternative geometries. For example, cavity 18 could define a rectangular and/or square cross-section, a hexagonal cross-section, an elliptical cross-section, or an irregular cross-section.

The bottom electrode 22 is typically insulated on its cavity-facing surface with an additional layer (not pictured). A preferred insulating layer is an oxide-nitride-oxide (ONO) dielectric layer formed above the substrate electrode and below the membrane electrode. The ONO-dielectric layer advantageously reduced charge accumulation on the electrodes which leads to device instability and drift and reduction in acoustic output pressure. The fabrication of ONO-dielectric layers on a CMUT is discussed in detail in European patent application no. 08305553.3 by Klootwijk et al., filed Sep. 16, 2008 and entitled "Capacitive micromachined ultrasound transducer." Use of the ONO-dielectric layer is desirable with collapsed mode CMUT, which are more susceptible to charge retention than are uncollapsed device. The disclosed components may be fabricated from CMOS compatible materials, e.g., Al, Ti, nitrides (e.g., silicon nitride), oxides (various grades), tetra ethyl oxysilane (TEOS), poly-silicon and the like. In a CMOS fab, for example, the oxide and nitride layers may be formed by chemical vapor deposition and the metallization (electrode) layer put down by a sputtering process. Suitable CMOS processes are LPCVD and PECVD, the latter having a relatively low operating temperature of less than 400° C.

Exemplary techniques for producing the disclosed cavity 18 involve defining the cavity in an initial portion of the membrane layer 14 before adding a top face of the membrane layer 14. Other fabrication details may be found in U.S. Pat. No. 6,328,697 (Fraser). In the exemplary embodiment depicted in FIG. 2, the diameter of the cylindrical cavity 18 is larger than the diameter of the circularly configured electrode plate 22. Electrode ring 28 may have the same outer diameter as the circularly configured electrode plate 22, although such conformance is not required. Thus, in an exemplary embodiment of the present invention, the electrode ring 28 is fixed relative to the top face of the membrane layer 14 so as to align with the electrode plate 22 below.

In FIG. 2 the CMUT cell membrane layer is biased to a collapsed state, in which the membrane 14 is in contact with the floor of the cavity 18. This is accomplished by applying a DC bias voltage to the two electrodes as indicated by voltage $V_B$ applied to the electrode ring 28 and a reference potential (ground) applied to the substrate electrode 22. In a preferred implementation of a CMUT cell of the present invention, the bottom electrode is not grounded but coupled to a DC reference potential and the a.c. drive signal for the cell (as well as received signals) are applied to and received at the bottom electrode. This electrode arrangement improves patient safety by moving a high voltage potential of the relatively high DC bias voltage further away from the patient-facing side. While the electrode ring 28 could also be formed as a continuous disk without the hole in the center, FIG. 2 illustrates why this is not necessary. When the membrane 14 is biased to its precollapsed (or fully collapsed) state as shown in this drawing, the center of the membrane is in contact with the floor of the cavity 18. As such, the center of the membrane 14 does not move during operation of the CMUT. Rather, it is the peripheral area of the membrane 14 which moves, that which is above the remaining open void of the cavity 18 and below the ring electrode. By forming the membrane electrode 28 as a ring, the charge of the upper plate of the capacitance of the device is located above the area of the CMUT which exhibits the motion and capacitive variation when the CMUT is operating as a transducer. Thus, the coupling coefficient of the CMUT transducer is improved.

Figure 3:
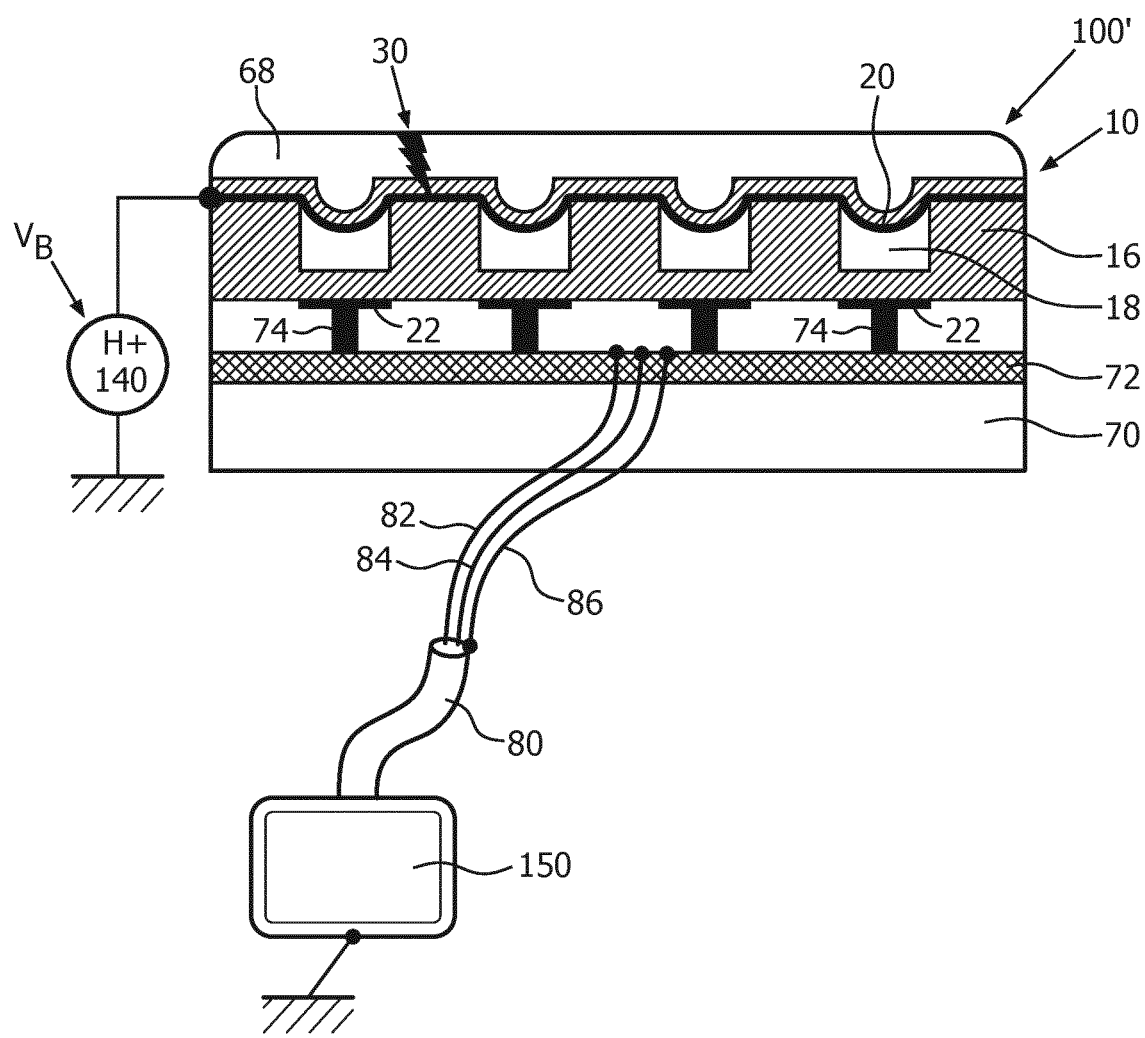
FIG. 3 is a cross-sectional view of a CMUT array coupled to an ultrasound system which illustrates the hazard presented by a crack in the insulating lens material of a CMUT probe.

FIG. 3 illustrates a CMUT transducer probe 100' connected to an ultrasound system represented at 150 in the drawing. Shown in this illustration is an array of four CMUT cells 10 with a common top electrode 20 and individual bottom electrodes 22 for each CMUT cell. Dielectric 16 supports the top electrodes and membranes across the cavity 18 of each cell which allows the membranes and top electrodes to move in response to an applied DC bias voltage $V_B$ and received ultrasonic energy. A DC bias voltage H+ ($V_B$) is applied to the common electrode 20 to bias the top electrodes in the desired proximity with the floors of the cavities 18. The exact value of the DC bias voltage required to bring the membrane in the proximity of the cavity floor (into a pre-collapsed or collapsed state) may depend on the CMUT's cell exact design and dimensions. The CMUT cells, having an average diameter of about 70 micrometer, may require an application of the DC bias voltage of around 150 V in order to bring the cell membrane in the proximity of the cell floor. Therefore, a range of voltages within which the CMUT array may operate can be a range of the relatively high DC bias voltages being above 50V or even above 100-150V. A lens 68 or other insulative covering protects the patient from direct contact with the high voltage of the DC bias. In accordance with a preferred implementation of the present invention the CMUT cells are fabricated on a substrate 70 of an ASIC of control integrated circuitry 72 for the CMUT cells. The bottom electrodes 22 of the CMUT cells are electrically connected to the circuitry of the ASIC by vias 74 through the top surface of the substrate 70. Alternatively the CMUT can be formed on its own substrate 12 and connected to a separate ASIC through any of a number of techniques known to those skilled in the art such as flip chip connection, conductive adhesives, or through silicon vias. The ASIC circuitry of the CMUT probe is connected to the ultrasound system 150 by a cable 80 which has one end coupled to the ASIC circuitry and the other end coupled by a probe connector to ultrasound system 150. The ultrasound system controls the transducer (probe) electronics of the ASIC through analog or digital control lines 82, which transmit control signals to the array, in the cable and receives ultrasound signals through analog or digital signal lines 84, which transmit ultrasound signals from the array. The shielding 86 of the cable 80 is coupled to the ASIC so that the reference potential of the ASIC is the same ground reference as that of the ultrasound system.

FIG. 3 illustrates the problem addressed by the present invention, which is that a crack 30 has developed in the insulating lens material 68, extending from the patient-contacting upper surface of the lens to the CMUTs below and their top electrodes 20 which are biased to the high voltage H+ suppled from the DC bias voltage supply 140, which is usually around 100 volts. This means that the patient is exposed to the high voltage through the acoustic couplants commonly used with the probe and the hazard of a high voltage shock.

Figure 4:
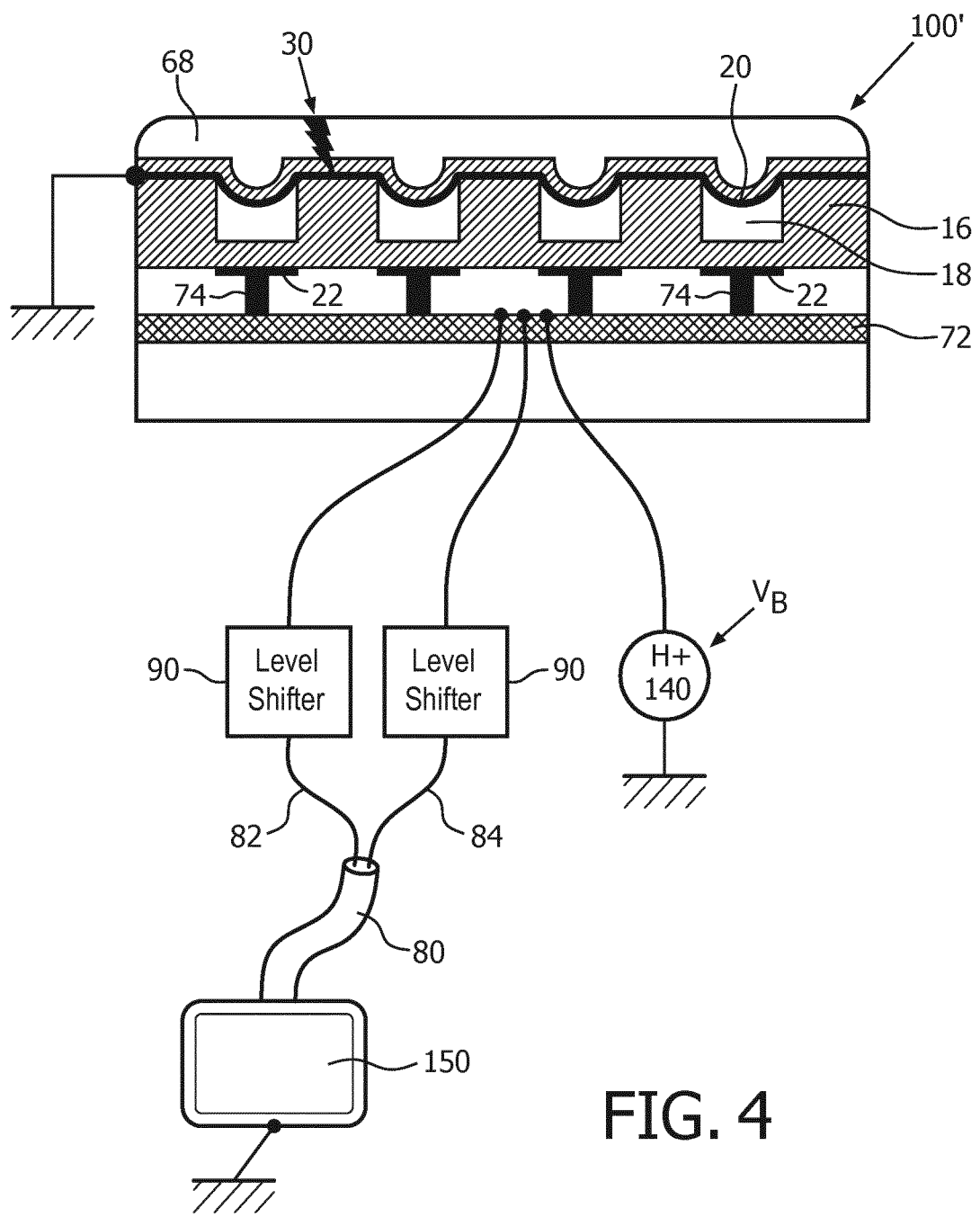
FIG. 4 is a cross-sectional view of a CMUT array coupled to an ultrasound system in accordance with the principles of the present invention with the membrane electrodes grounded and the probe electronics floating with level shifted signal connections.

FIG. 4 illustrates the same CMUT probe 100' and ultrasound system 150 configuration but with the bias voltage $V_B$ applied for improved patient safety in accordance with the present invention. Instead of applying the high voltage bias $V_B$ from the bias supply to the top membrane electrodes of the CMUT cells, a low voltage which does not pose a shock hazard or ground is coupled to the top membrane electrodes as shown in the drawing. The high voltage side of the bias potential is then applied at the bottom electrodes of the CMUT cells as shown by the H+ supply 140 connection to the ASIC circuitry 72 (probe electronics). However, this creates a problem which is that the low voltage ASIC circuitry 72 must now operate with reference to the high potential of the H+ supply. Furthermore, the control signal lines from the ultrasound system operate at low voltages belonging to a range of the relatively low voltages (this is the voltage range of the ultrasound system operation) and therefore cannot be directly connected to the ASIC circuitry, which is now floating at the high voltage potential. In accordance with a further aspect of the present invention, control signals are coupled between the ultrasound system 150 and the ASIC circuitry by level shifters, which provide DC isolation in the control signal lines and shift the signal baseline to that of the electrically floating ASIC circuitry. One or more level shifters 90 are used to make the shifted signal coupling through the digital control lines 82, and are also used to couple analog signals such as received ultrasound signals through the signal lines 84. These level shifters can be adapted to shift a baseline of the control signal from a relatively low or reference voltage to a range of the relatively high DC bias voltage, which is coupled to the bottom electrodes of the CMUT cells. Further, these level shifters can be adapted to shift a baseline of the ultrasound signals provided by the probe circuitry 72 (ASIC) from the high voltage potential to the range of the relatively low voltage potential (which can be the reference potential of the ultrasound system). Thus the high DC bias voltage is applied in a way which can only expose the patient to a harmless electrical potential in the event of failure of the insulating lens, the ASIC electronics 72 is operated by electrically floating it relative to the high potential of the bias voltage, and there is no DC coupling of control through the probe cable 80 to the ASIC electronics, which instead are level shifted to the reference high voltage on the ASIC circuitry. In addition, the baseline of the ultrasound signals transmitted to the ultrasound system is shifted to the range of the relatively low voltages, within which the system is arranged to operate. Thus, level shifters provide a further decoupling of the ultrasound system electronics from the high DC voltages of the probe. A combination of the level shifters with the floating probes electronics provides not only improved patience safety but also a simplified electrical arrangement. The range of the relatively high DC bias voltage has the relatively high DC bias voltage located in its middle and expands into increasing and reduced voltage values with respect to the relatively high DC bias voltage. For example, the range can be 25% or 20%, preferably 5% of a total voltage difference between the relatively low (or reference voltage) and the relatively high DC bias voltage. The range of the relatively low voltages can be in the order of 5 to 20 V; or 0 to 10 V; while the range of the relatively high DC relatively high DC bias voltage can be 50 to 70 V; or 100 to 160 V. The level shifter(s) 90 can be located at the connector end of the probe cable in the connector enclosure, in the handle of the probe, or integrated into the electronics behind the CMUT array as is the ASIC electronics.

Figure 5A:
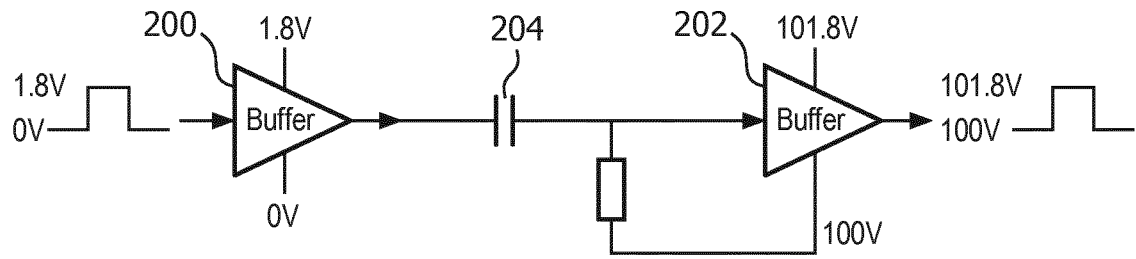
FIGS. 5a-5d illustrate level shifters suitable for use in the implementation of the present invention of FIG. 4 for coupling digital control signals between the CMUT probe and the ultrasound system.

FIGS. 5a-5d illustrate several level shifter configurations suitable for use for level shifters 90 in FIG. 4 for shifting the level of digital signals. FIG. 5a shows a pulse from 1.8 v digital circuitry being applied to the input of a buffer amplifier 200, which is referenced between 0 v for a grounded ultrasound system and a 1.8 v supply. The output signals of the buffer amplifier are capacitively coupled by a capacitor 204 to the input of a second buffer amplifier 202, which is referenced between 100 v and 101.8 v. The output signals of buffer amplifier 202 are the same as the original input signals, but now referenced to 100 v (the voltage of the H+ bias supply in this example) for the 1.8 v signal amplitude, which is now at 101.8 v. This circuit accomplishes level shifting using a capacitor 204.

Figure 5B:
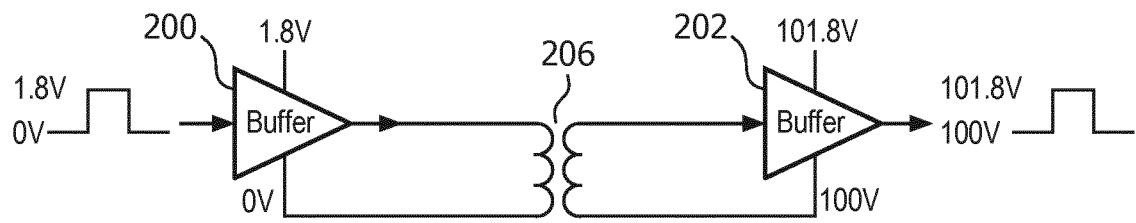

FIG. 5b illustrates another level shifter configuration which uses a transformer 206. The primary winding of the transformer is driven by buffer amplifier 200 and the secondary signal is stepped up to a 100v reference level. As a result, buffer amplifier 202 will again produce the original 1.8 v digital pulse but now varying between 101.8 v and the 100 v reference level.

Figure 5C:
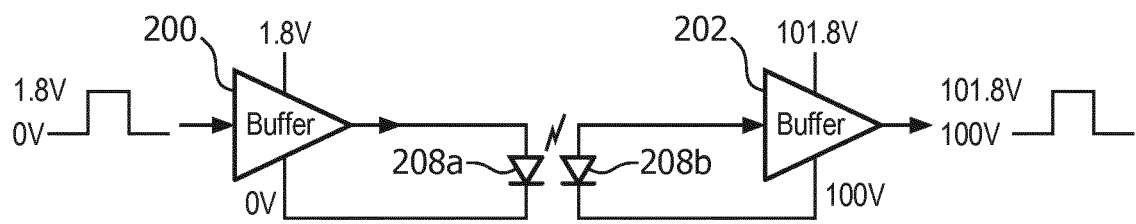

FIG. 5c illustrates an optical level shifter configuration, this one using a pair of photo diodes 208. Photo diode 208a is driven by buffer amplifier 200 to emit a pulse of light, which is received by photo diode 208b. The electrical signal of receiving photo diode 208b is referenced to 100 v by operation of the buffer amplifier 202 referenced between 100 v and 101.8 v, which is again the amplitude variation of the output signal referenced to 100 v.

Figure 5D:
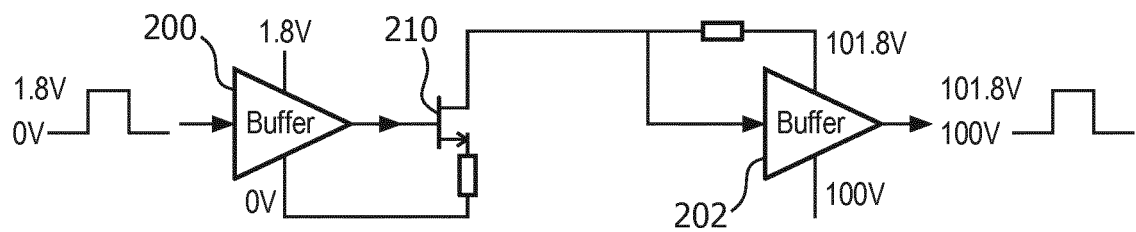

FIG. 5d illustrates another level shifter configuration, this time using a transistor 210 and taking advantage of the high input impedance at the base (with use of a bipolar junction transistor) or gate (with use of a FET) electrode of the transistor. The illustrated transistor is driven by the buffer amplifier 200 with its output collector (or drain in the FET case) electrode coupled to the 101.8 v supply for buffer amplifier 202. The buffer amplifier 202 again produces a 1.8 v output signal referenced to 100 v (100 v→101.8 v).

Figure 6A:
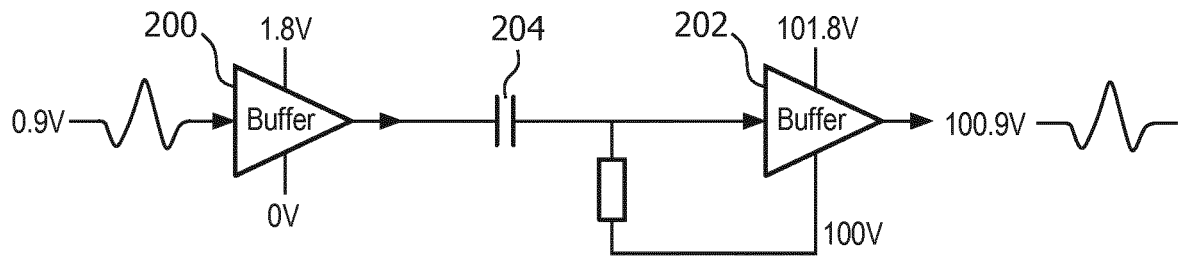
FIGS. 6a-6c illustrate level shifters suitable for use in the implementation of the present invention of FIG. 4 for coupling analog ultrasound signals between the CMUT probe and the ultrasound system.
Figure 6B:
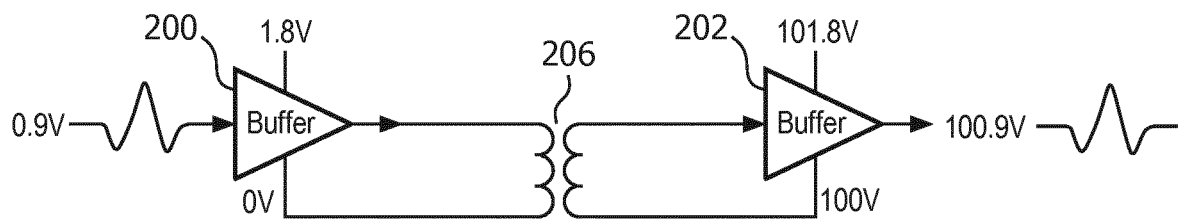
Figure 6C:
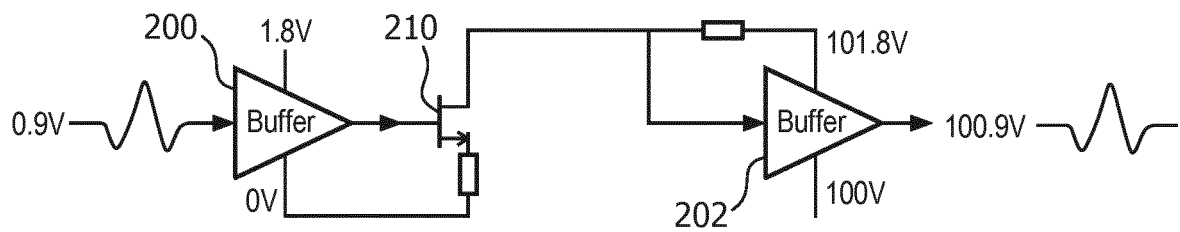

FIGS. 6a, 6b and 6c illustrate several of the level shifter configurations of FIG. 5, this time being used for level shifting an analog signal. In these examples the input signal is an analog signal varying about a 0.9 v reference level. As a result of level shifting using a capacitor 204 (FIG. 6a), a transformer 206 (FIG. 6b) or a transistor 210 (FIG. 6c), the output buffer amplifier 202 produces the same 1.8 v peak-to-peak analog signal as the input signal but now baselined to 100.9 v, varying between a maximum excursion of 100 v and 101.8 v in each example.

Figure 7:
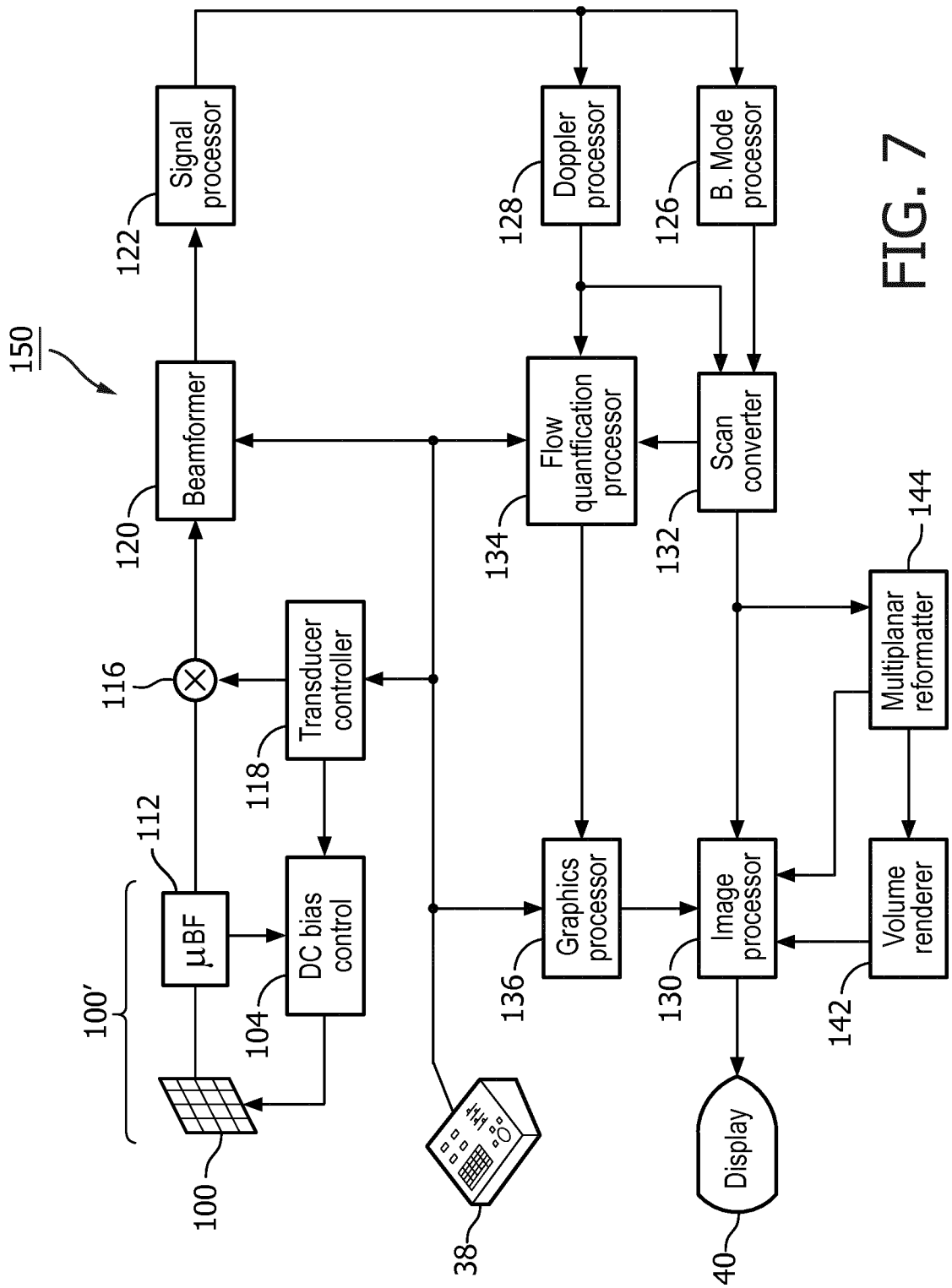
FIG. 7 is a block diagram of an ultrasonic imaging system suitable for use with CMUT probe of the present invention.

FIG. 7 illustrates in block diagram form an ultrasonic diagnostic imaging system 150 suitable for use with a CMUT array probe of the present invention. A CMUT array 100 is located on the tip of a catheter or distal end of an ultrasound probe 100', together with a microbeamformer ASIC 112. The microbeamformer ASIC 112 may comprise control integrated circuitry 72 for the CMUT cells. The CMUT array 100 can be a one- or a two-dimensional array of MUT transducer elements capable of scanning in a 2D plane or in three dimensions for 3D imaging. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.) The microbeamformer is coupled to transmit/receive (T/R) switches 116 which switch between transmission and reception and protect the main system beamformer 120 from high energy transmit signals when a microbeamformer is not used and a transducer array is operated directly by the main system beamformer. The transmission of ultrasonic beams from the CMUT transducer array 100 under control of the microbeamformer ASIC 112 is directed by a transducer controller 118 coupled to the T/R switch and the main system beamformer 120, which receives input from the user's operation of the user interface or control panel 38. One of the functions controlled by the transducer controller is the direction in which beams are steered. Beams may be steered straight ahead from (orthogonal to) the transducer array, or at different angles for a wider field of view. The transducer controller 118 also controls a circuit 104 for the DC bias applied from the DC bias supply 140 to the CMUT cells which biases the cell membranes 14 as described above to a partially or fully collapsed state for operation of the CMUTs in the desired mode of operation.

The partially beamformed signals produced by the microbeamformer 112 on receive are coupled to a main beamformer 120 where partially beamformed signals from individual patches of transducer elements are combined into a fully beamformed signal. For example, the main beamformer 120 may have 128 channels, each of which receives a partially beamformed signal from a patch of dozens or hundreds of CMUT transducer cells. In this way the signals received by thousands of transducer elements of a CMUT transducer array can contribute efficiently to a single beamformed signal. In a basic implementation the acoustic signals received from rows of CMUT cells are processed into beams from an image plane in front of the rows of cells to form a scanned 2D image.

The beamformed signals are coupled to a signal processor 122. The signal processor 122 can process the received echo signals in various ways, such as bandpass filtering, decimation, I and Q component separation, and harmonic signal separation which acts to separate linear and nonlinear signals so as to enable the identification of nonlinear echo signals returned from tissue and microbubbles. The signal processor may also perform additional signal enhancement such as speckle reduction, signal compounding, and noise elimination. The bandpass filter in the signal processor can be a tracking filter, with its passband sliding from a higher frequency band to a lower frequency band as echo signals are received from increasing depths, thereby rejecting the noise at higher frequencies from greater depths where these frequencies are devoid of anatomical information.

The processed signals are coupled to a B mode processor 126 and a Doppler processor 128. The B mode processor 126 employs amplitude detection for the imaging of structures in the body such as the tissue of organs and vessels in the body. B mode images of structure of the body may be formed in either the harmonic mode or the fundamental mode or a combination of both as described in U.S. Pat. No. 6,283,919 (Roundhill et al.) and U.S. Pat. No. 6,458,083 (Jago et al.) The Doppler processor 128 processes temporally distinct signals from tissue movement and blood flow for the detection of the motion of substances such as the flow of blood cells in the image field. The Doppler processor typically includes a wall filter with parameters which may be set to pass and/or reject echoes returned from selected types of materials in the body. For instance, the wall filter can be set to have a passband characteristic which passes signal of relatively low amplitude from higher velocity materials while rejecting relatively strong signals from lower or zero velocity material. This passband characteristic will pass signals from flowing blood while rejecting signals from nearby stationary or slowing moving objects such as the wall of the heart. An inverse characteristic would pass signals from moving tissue of the heart while rejecting blood flow signals for what is referred to as tissue Doppler imaging, detecting and depicting the motion of tissue. The Doppler processor receives and processes a sequence of temporally discrete echo signals from different points in an image field, the sequence of echoes from a particular point referred to as an ensemble. An ensemble of echoes received in rapid succession over a relatively short interval can be used to estimate the Doppler shift frequency of flowing blood, with the correspondence of the Doppler frequency to velocity indicating the blood flow velocity. An ensemble of echoes received over a longer period of time is used to estimate the velocity of slower flowing blood or slowly moving tissue.

The structural and motion signals produced by the B mode and Doppler processors are coupled to a scan converter 132 and a multiplanar reformatter 144. The scan converter arranges the echo signals in the spatial relationship from which they were received into a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field corresponding with their Doppler-estimated velocities to produce a color Doppler image which depicts the motion of tissue and blood flow in the image field. The multiplanar reformatter will convert echoes which are received from points in a common plane in a volumetric region of the body into an ultrasonic image of that plane, as described in U.S. Pat. No. 6,443,896 (Detmer). A volume renderer 142 converts the echo signals of a 3D data set into a projected 3D image as viewed from a given reference point as described in U.S. Pat. No. 6,530,885 (Entrekin et al.) The 2D or 3D images are coupled from the scan converter 32, multiplanar reformatter 44, and volume renderer 142 to an image processor 130 for further enhancement, buffering and temporary storage for display on an image display 40. In addition to being used for imaging, the blood flow velocity values produced by the Doppler processor 128 are coupled to a flow quantification processor 134. The flow quantification processor produces measure of different flow conditions such as the volume rate of blood flow. The flow quantification processor may receive input from the user control panel 38, such as the point in the anatomy of an image where a measurement is to be made. Output data from the flow quantification processor is coupled to a graphics processor 136 for the reproduction of measurement values with the image on the display 40. The graphics processor 136 can also generate graphic overlays for display with the ultrasound images. These graphic overlays can contain standard identifying information such as patient name, date and time of the image, imaging parameters, and the like. For these purposes the graphics processor receives input from the user interface 38, such as a typed patient name. The user interface is also coupled to the transducer controller 118 to control the generation of ultrasound signals from the transducer array 100 and hence the images produced by the transducer array and the ultrasound system. The user interface is also coupled to the multiplanar reformatter 144 for selection and control of a display of multiple multiplanar reformatted (MPR) images which may be used to perform quantified measures in the image field of the MPR images.

The invention claimed is:

1. A capacitive micromachined ultrasonic transducer (CMUT) array probe with improved patient safety, the CMUT array probe being connectable to an ultrasound system operating in a first range of voltages, wherein the CMUT array probe comprises:
- a substrate;
- a plurality of CMUT cells located on the substrate, each of the plurality of CMUT cells having a top patient-facing electrode and a bottom electrode, wherein the plurality of CMUT cells is configured to operate in a second range of voltages different than the first range of voltages, wherein the second range of voltages comprise:
  - a reference voltage is applied to the top patient-facing electrode of each of the plurality of CMUT cells; and
  - a DC bias voltage is applied to the bottom electrode of each of the plurality of CMUT cells, wherein the DC bias voltage is higher than the reference voltage and voltages in the first range of voltages;
- probe electronics coupled to the plurality of CMUT cells and arranged to provide control signals to the plurality of CMUT cells and ultrasound signals from the plurality of CMUT cells, wherein the probe electronics comprise an application specific integrated circuit (ASIC) electrically coupled to the DC bias voltage, wherein the ASIC is configured to electrically float relative to the DC bias voltage;
- a probe cable having a first end coupled to the probe electronics and a second end coupleable to the ultrasound system and having a control signal line and an ultrasound signal line, wherein the control signal line is adapted to transmit the control signals within the first range voltages from the ultrasound system to the probe electronics and the ultrasound signal line is adapted to transmit the ultrasound signals within the second range of voltages from the probe electronics to the ultrasound system; and
- one or more level shifters coupled to the control signal line and the ultrasound signal line, wherein the one or more level shifters is adapted to shift a baseline of the control signals from the first range of voltages to the second range of voltages and to shift a baseline of the ultrasound signals from the second range of voltages to the first range of voltages.

2. The CMUT array probe of claim 1, wherein the one or more level shifters further comprise a capacitive level shifter, a transformer level shifter, an optical level shifter, or a transistor level shifter.

3. The CMUT array probe of claim 2, wherein the one or more level shifters further comprises first and second buffers interposed by a capacitor, first and second buffers interposed by a transformer, first and second buffers interposed by photo diodes, or first and second buffers interposed by a transistor.

4. The CMUT array probe of claim 1, wherein the ASIC is located on the substrate.

5. The CMUT array probe of claim 1, further comprising a second substrate; wherein the ASIC is located on the second substrate.

6. The CMUT array probe of claim 5, wherein the ASIC on the second substrate is electrically coupled to the plurality of CMUT cells on the substrate by a flip chip connection, conductive adhesive, or through silicon vias.

7. The CMUT array probe of claim 1, wherein the one or more level shifters are located at the second end of the probe cable.

8. The CMUT array probe of claim 1, wherein the one or more level shifters are located in a handle of the CMUT array probe.

9. The CMUT array probe of claim 8, wherein the one or more level shifters are integrated into the probe electronics.

10. The CMUT array probe of claim 1, wherein the ultrasound signal line further comprises an analog signal line.

11. The CMUT array probe of claim 1, wherein the DC bias voltage further comprises a DC bias supply coupled between the probe electronics and ground.

12. The CMUT array probe of claim 11, further comprising:
- a probe housing; and
- a DC bias control circuit configured to control the DC bias supply, wherein the DC bias control circuit is positioned within the probe housing.

13. The CMUT array probe of claim 1, further comprising an insulating covering overlaying the top patient-facing electrode of each of the plurality of CMUT cells.

14. The CMUT array probe of claim 13, wherein the insulating covering further comprises an acoustic lens.

15. The CMUT array probe of claim 1,
- wherein each of the plurality of CMUT cells comprises a cell membrane, and
- wherein, for each of the plurality of CMUT cells, the bottom electrode is configured to bias the cell membrane to operate in a collapsed state based on the DC bias voltage.

16. The CMUT array probe of claim 1, further comprising a probe housing, wherein the ASIC is positioned within the probe housing.

17. The CMUT array probe of claim 1, wherein the ASIC comprises microbeamformer circuitry.

* * * * *